(12) United States Patent
Eidenschink et al.

(10) Patent No.: US 8,025,636 B2
(45) Date of Patent: Sep. 27, 2011

(54) BALLOON CATHETERS

(75) Inventors: Tracee Eidenschink, Wayzata, MN (US); Matt Heidner, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 502 days.

(21) Appl. No.: 11/743,255

(22) Filed: May 2, 2007

(65) Prior Publication Data

US 2008/0275390 A1 Nov. 6, 2008

(51) Int. Cl.
*A61M 29/00* (2006.01)
(52) U.S. Cl. ................... 604/96.01; 606/191
(58) Field of Classification Search .......... 604/96.01, 604/103.01–103.02, 103.06–103.08; 623/1.11; 606/191–195
See application file for complete search history.

(56) References Cited

U.S. PATENT DOCUMENTS

| | | | |
|---|---|---|---|
| 5,226,887 A | 7/1993 | Farr et al. .............. 604/96 |
| 5,318,587 A | 6/1994 | Davey ................ 606/194 |
| 5,425,710 A | 6/1995 | Khair et al. ............. 604/96 |
| 5,456,666 A | 10/1995 | Campbell et al. ......... 604/96 |
| 5,458,572 A | 10/1995 | Campbell et al. ......... 604/96 |
| 5,478,319 A | 12/1995 | Campbell et al. ......... 604/96 |
| 5,512,051 A | 4/1996 | Wang et al. ............. 604/96 |
| 5,573,520 A * | 11/1996 | Schwartz et al. ......... 604/526 |
| 5,643,209 A | 7/1997 | Fugoso et al. ........... 604/96 |
| 5,681,281 A * | 10/1997 | Vigil et al. .......... 604/103.01 |
| 5,720,726 A | 2/1998 | Maracdis et al. |
| 5,769,817 A | 6/1998 | Burgmeier ............. 604/96 |
| 5,871,468 A | 2/1999 | Kramer et al. ............ 604/96 |
| 5,891,386 A | 4/1999 | Deitermann et al. ....... 264/526 |
| 5,964,778 A | 10/1999 | Fugoso et al. ............ 60/194 |
| 6,013,055 A | 1/2000 | Bampos et al. ........... 604/96 |
| 6,048,356 A | 4/2000 | Ravenscroft et al. ...... 606/194 |
| 6,071,285 A | 6/2000 | Lashinski et al. ........ 606/108 |
| 6,124,007 A | 9/2000 | Wang et al. ............. 428/35.2 |
| 6,126,652 A | 10/2000 | McLeod et al. ............ 606/1 |
| 6,129,737 A | 10/2000 | Hamilton et al. ........ 606/194 |
| 6,187,014 B1 | 2/2001 | Goodin et al. .......... 606/108 |
| 6,283,743 B1 | 9/2001 | Traxler et al. .......... 425/391 |
| 6,328,925 B1 | 12/2001 | Wang et al. ............ 264/512 |
| 6,465,067 B1 | 10/2002 | Wang et al. ........... 428/35.7 |
| 6,488,688 B2 | 12/2002 | Lim et al. ............. 606/108 |
| 6,491,711 B1 | 12/2002 | Durcan ............... 606/194 |
| 6,540,734 B1 | 4/2003 | Chiu et al. ............. 604/508 |
| 6,589,274 B2 | 7/2003 | Stiger et al. ........... 623/1.11 |
| 6,623,451 B2 | 9/2003 | Vigil .................. 604/99.01 |
| 6,623,689 B2 | 9/2003 | Traxler et al. .......... 264/573 |
| 6,645,422 B2 | 11/2003 | Jung, Jr. et al. ........ 264/530 |
| 6,696,121 B2 | 2/2004 | Jung, Jr. et al. ........ 428/35.7 |

(Continued)

FOREIGN PATENT DOCUMENTS

EP 0275230 7/1988

(Continued)

*Primary Examiner* — Nicholas D Lucchesi
*Assistant Examiner* — Rebecca E Eisenberg
(74) *Attorney, Agent, or Firm* — Vidas, Arrett & Steinkraus, P.A.

(57) ABSTRACT

A method of using a balloon catheter, comprising the steps of providing a balloon catheter, the balloon catheter comprising a balloon and a plurality of fins, the plurality of fins engaged to the balloon; inserting the balloon catheter into the vasculature; advancing the balloon catheter through the vasculature to a desired location; inflating the balloon when the balloon catheter is at the desired location; deflating the balloon; and directing the blood flow along the balloon thereby aiding rewrap.

16 Claims, 11 Drawing Sheets

U.S. PATENT DOCUMENTS

| | | | |
|---|---|---|---|
| 6,706,010 B1 | 3/2004 | Miki et al. | 604/43 |
| 6,733,520 B2 | 5/2004 | Yang et al. | 623/1.12 |
| 7,163,504 B1 | 1/2007 | Chiu et al. | 600/3 |
| 2001/0001113 A1 | 5/2001 | Lim et al. | 604/96.01 |
| 2001/0008661 A1 | 7/2001 | Jung, Jr. et al. | 428/35.5 |
| 2001/0056273 A1* | 12/2001 | C. | 604/509 |
| 2002/0041940 A1 | 4/2002 | Jung, Jr. et al. | 428/35.2 |
| 2002/0087165 A1 | 7/2002 | Lee et al. | 606/108 |
| 2003/0055378 A1 | 3/2003 | Wang et al. | 604/103.07 |
| 2003/0074044 A1 | 4/2003 | Randby et al. | 623/1.11 |
| 2003/0088209 A1 | 5/2003 | Chiu et al. | 604/96.01 |
| 2003/0171799 A1 | 9/2003 | Lee et al. | 623/1.11 |
| 2003/0176889 A1 | 9/2003 | Boyle et al. | 606/200 |
| 2004/0173935 A1 | 9/2004 | Lim et al. | 264/209.3 |
| 2004/0193252 A1 | 9/2004 | Perez et al. | 623/1.23 |
| 2005/0015046 A1 | 1/2005 | Weber et al. | 604/96.01 |
| 2005/0059989 A1 | 3/2005 | Eidenschink | 606/192 |
| 2005/0102020 A1* | 5/2005 | Grayzel et al. | 623/1.11 |
| 2005/0137620 A1 | 6/2005 | Alkhatib | 606/194 |
| 2005/0149161 A1 | 7/2005 | Eidenschink et al. | 623/1.11 |
| 2006/0015134 A1 | 1/2006 | Trinidad | 604/194 |
| 2006/0079836 A1 | 4/2006 | Holman et al. | |
| 2006/0182873 A1 | 8/2006 | Klisch et al. | |
| 2007/0112300 A1 | 5/2007 | Roman et al. | 604/103.07 |

FOREIGN PATENT DOCUMENTS

| | | | |
|---|---|---|---|
| EP | 0724891 | 7/1996 | |
| EP | 1254679 | 6/2002 | |
| GB | 1511557 | * 7/1975 | 604/264 |

* cited by examiner

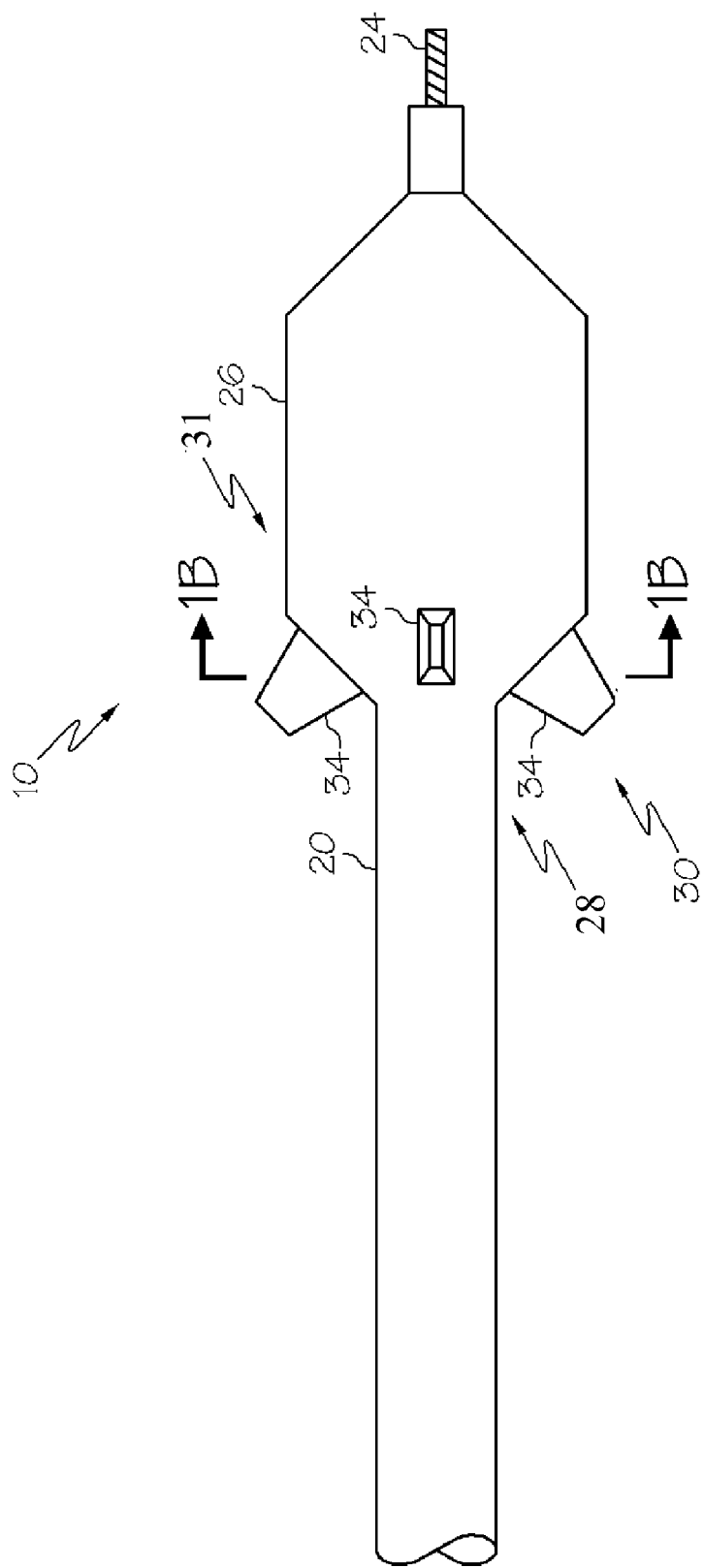

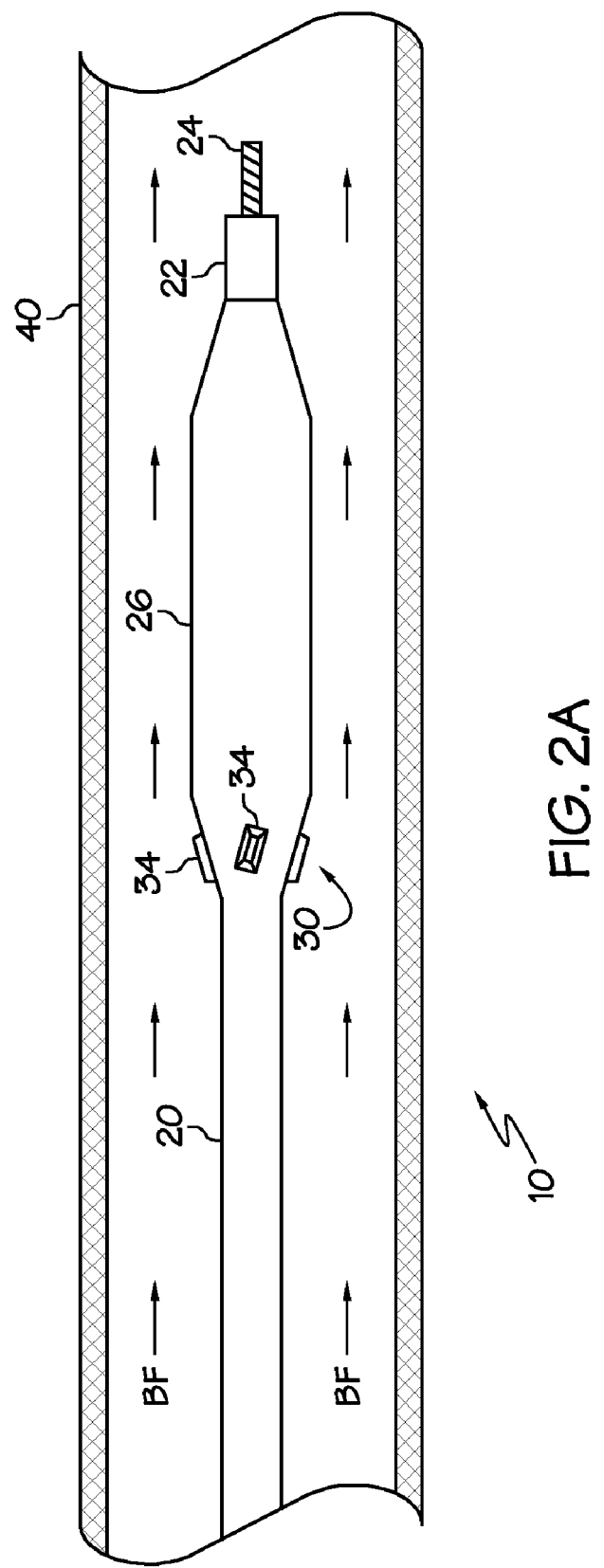

BALLOON CATHETERS

CROSS-REFERENCE TO RELATED APPLICATIONS

Not Applicable

STATEMENT REGARDING FEDERALLY SPONSORED RESEARCH

Not Applicable

FIELD OF THE INVENTION

In some embodiments this invention relates to delivery systems, such as catheter systems of all types, which are utilized in the delivery of such implantable medical devices.

BACKGROUND OF THE INVENTION

Percutaneous transluminal angioplasty (PTA), including percutaneous transluminal coronary angioplasty (PTCA), is a procedure which is well established for the treatment of blockages, lesions, stenosis, thrombus, etc. present in body lumens, such as the coronary arteries and/or other vessels.

Percutaneous angioplasty makes use of a dilatation balloon catheter, which is introduced into and advanced through a lumen or body vessel until the distal end thereof is at a desired location in the vasculature. Once in position across an afflicted site, the expandable portion of the catheter, or balloon, is inflated to a predetermined size with a fluid at relatively high pressures. By doing so the vessel is dilated, thereby radially compressing the atherosclerotic plaque of any lesion present against the inside of the artery wall, and/or otherwise treating the afflicted area of the vessel. The balloon is then deflated to a small profile so that the dilatation catheter may be withdrawn from the patient's vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To reduce restenosis and strength the area, a physician can implant an intravascular prosthesis for maintaining vascular patency, such as a stent, inside the artery at the lesion.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In at least one embodiment, the invention is directed to a balloon catheter with improved rewrapping. In at least one embodiment, the balloon catheter has a plurality of fins engaged to the balloon. In at least one embodiment, the balloon catheter has a plurality of fins engaged to the cone of the balloon. In at least one embodiment, the invention is directed to a balloon catheter with at least one tether engaged to the interior surface of the balloon and a plurality of flow channels positioned in the inner shaft. In at least one embodiment, a collar with flow channels is engaged to the inner shaft of a balloon catheter with at least one tether engaged to the interior surface of the balloon.

In at least one embodiment, the invention is directed to a method of using a balloon catheter with a plurality of fins engaged to the balloon. In at least one embodiment, the invention is direction to a method of using a balloon catheter with at least one tether engaged to the interior surface of the balloon and a plurality of flow channels positioned between the outer shaft and the inner shaft, the balloon or both the inner shaft and the balloon.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

FIG. 1a is a side view of a balloon catheter with a balloon that has fins.

FIG. 2a is a cross-section of the blood vessel with the balloon catheter of FIG. 1c where the balloon is in an uninflated state.

DETAILED DESCRIPTION OF THE INVENTION

Figure 1B:
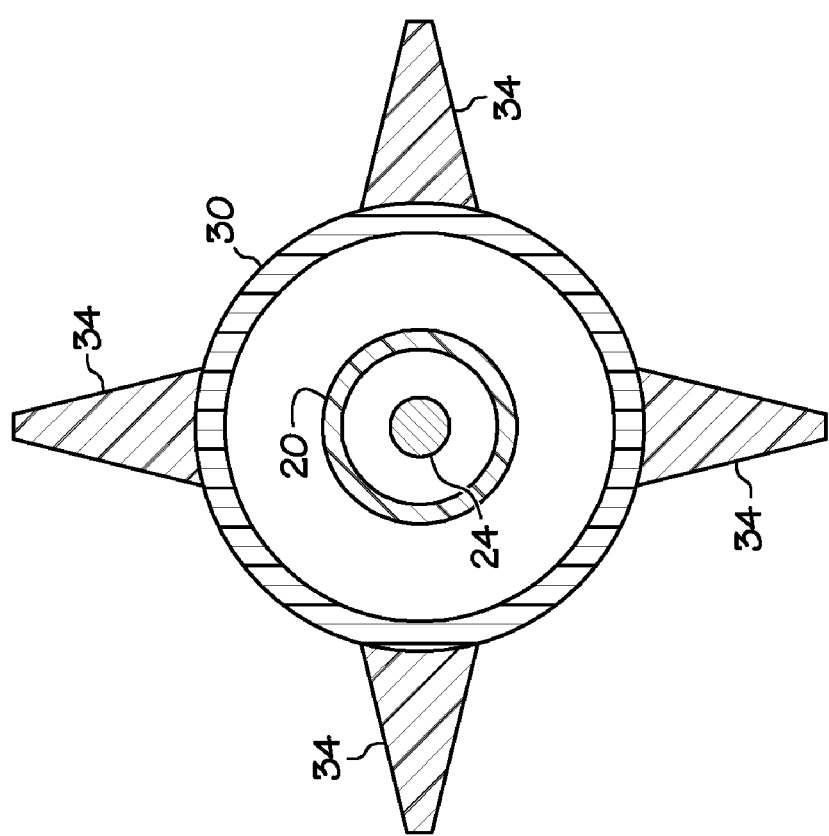
FIG. 1b is a cross-section of the balloon catheter of FIG. 1a taken at line 1b-1b.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

The catheters employed in the practice of the present invention are most conveniently constructed as over-the-wire balloon catheters of convention form for use in angioplasty. As shown the balloon catheter 10 comprises a balloon 26, an outer shaft 20, an inner shaft 16, a catheter tip 22, and a guidewire 24. However, it should be understood that the present invention can be applied, in addition to over-the-wire catheters, to fixed-wire catheters, to shortened guide wire lumens or single operator exchange catheters, and to non over-the-wire balloon catheters. Furthermore this invention can be used with balloon catheters intended for use in any and all vascular systems or cavities of the body.

FIGS. 1a and b illustrate an embodiment of the balloon catheter 10 with fins 34 engaged to the proximal cone 30 of the balloon 26. The fins 34 can have any configuration as long as they aid in the rewrap of the balloon 26, as discussed in greater detail below. In the embodiment shown in FIGS. 1a and 1b, each fin 34 has a bottom surface, a top surface and at least one side engaging the bottom surface and the top surface of the fin 34. It is within the scope of the invention for the fin 34 to have one, two, three, four, five, six, seven, eight, nine, ten, or more sides. In this embodiment, the bottom surface and the top surface of the fin 34 each have an area with the top surface area smaller than the bottom surface area. However it is within the scope of the invention for the top surface area to be smaller than, equal to, or greater than, the bottom surface area. The plurality of sides engaging the bottom surface and the top surface of the fin 34 are at an oblique angle to the longitudinal axis of the balloon catheter 10. As used in this application, an oblique angle is any angle between about 0 and about 180 degrees and includes 90 degrees.

Figure 1C:
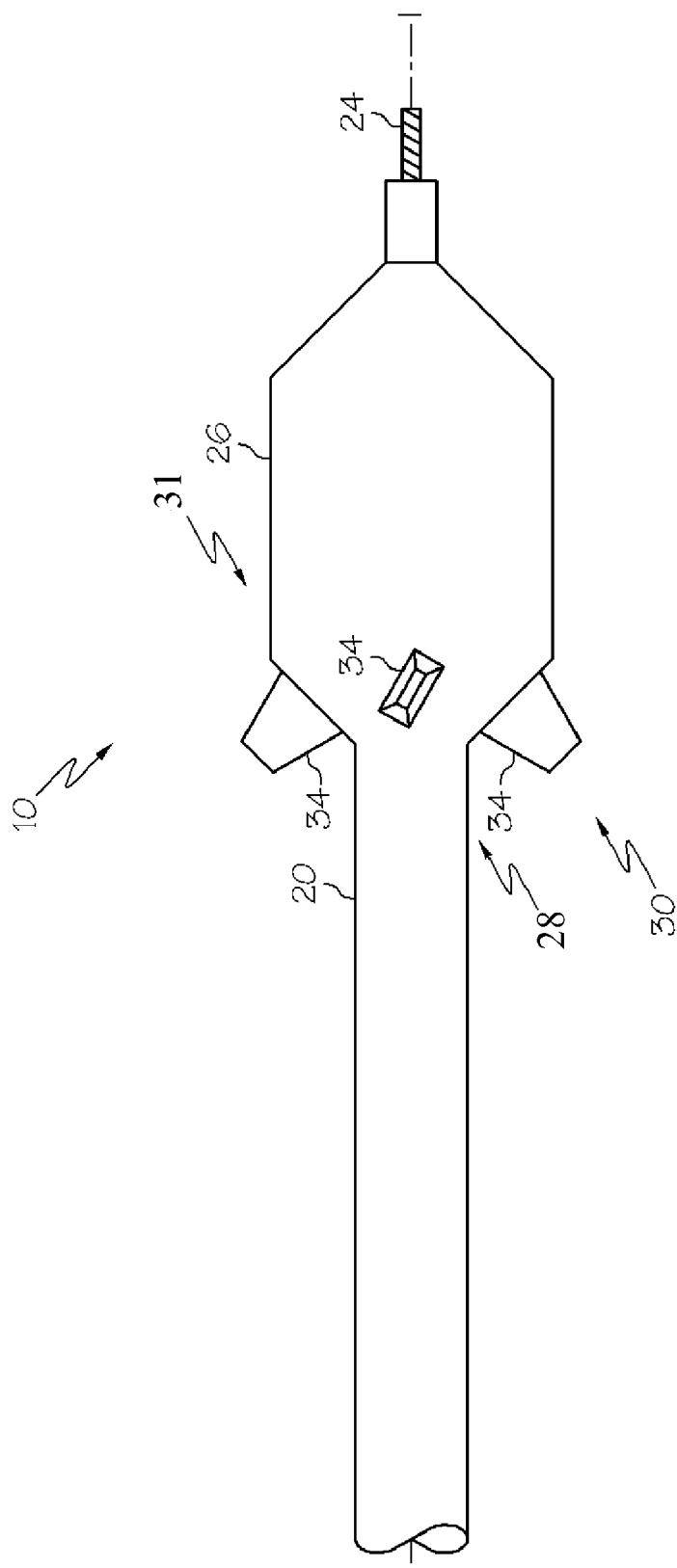
FIG. 1c is a side view of FIG. 1a with the fins at an angle to the longitudinal axis of the catheter.

It is within the scope of the invention for the bottom surface of the fins 34 to be engaged to at least one of the proximal cone 30, the proximal waist 28 or the proximal body 31 of the balloon 26. The fins 34 can be engaged to the exterior surface of the balloon 26 by any suitable means. Since the bottom surface of the fin 34 is engaged to the exterior surface of the balloon 26, the bottom surface of the fin 34 has a shape that is complementary to the shape of the exterior surface of the balloon 26. FIG. 1a is a side view of the distal end of the balloon catheter 10. The proximal cone 30 of the balloon 26 has fins 34 positioned about the circumference. It is within the scope of the invention for the fins 34 to have the same longitudinal position on the balloon 26 or for at least one fin 34 to have a different longitudinal position on the balloon 26 than the other fins 34. In this embodiment, there are four fins 34 which are parallel to the longitudinal axis of the balloon catheter 10. In FIG. 1c, the fins 34 are at an oblique angle to the longitudinal axis (1) of the balloon catheter 10. It is within the scope of the invention for there to be two, three, four, five, six or more fins 34 about the circumference of the proximal cone 30 of the balloon 26. FIG. 1b is a cross-section of the balloon 26 of FIG. 1a taken at line 1b-1b.

In at least one embodiment, the fins 34 are manufactured with semi-compliant material, for example, but not limited to, ethylene-vinyl acetate, polyvinyl chloride(PVC), olefin copolymers or homopolymers, polyethylenes, polyurethanes, crosslinked low density polyethylenes (PETs), highly irradiated linear low density polyethylene (LDPE), acrylonitrile polymers and copolymers, acrylonitrile blends and ionomer resins. In at least one embodiment, the fins 34 are manufactured with non-compliant material, for example, but not limited to, polyethylene terephthalates, polyacrylenesulfide, and copolyesters. In at least one embodiment, the fins 34 are manufactured with compliant material, for example, but not limited to, nylon, and polyamines. In at least one embodiment, the fins 34 and the balloon 26 are manufactured from the same material.

Figure 2B:
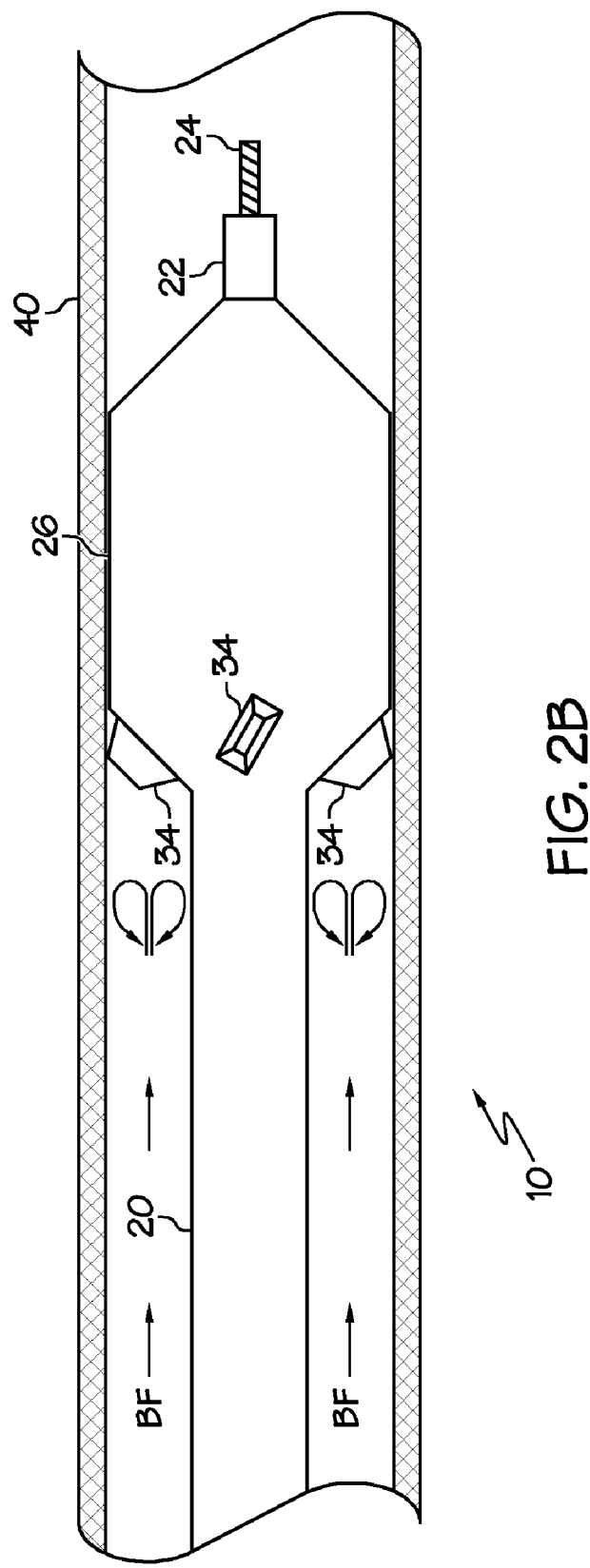
FIG. 2b is a cross-section of FIG. 2a with the balloon in an inflated state and the blood flow forming an eddy.
Figure 2C:
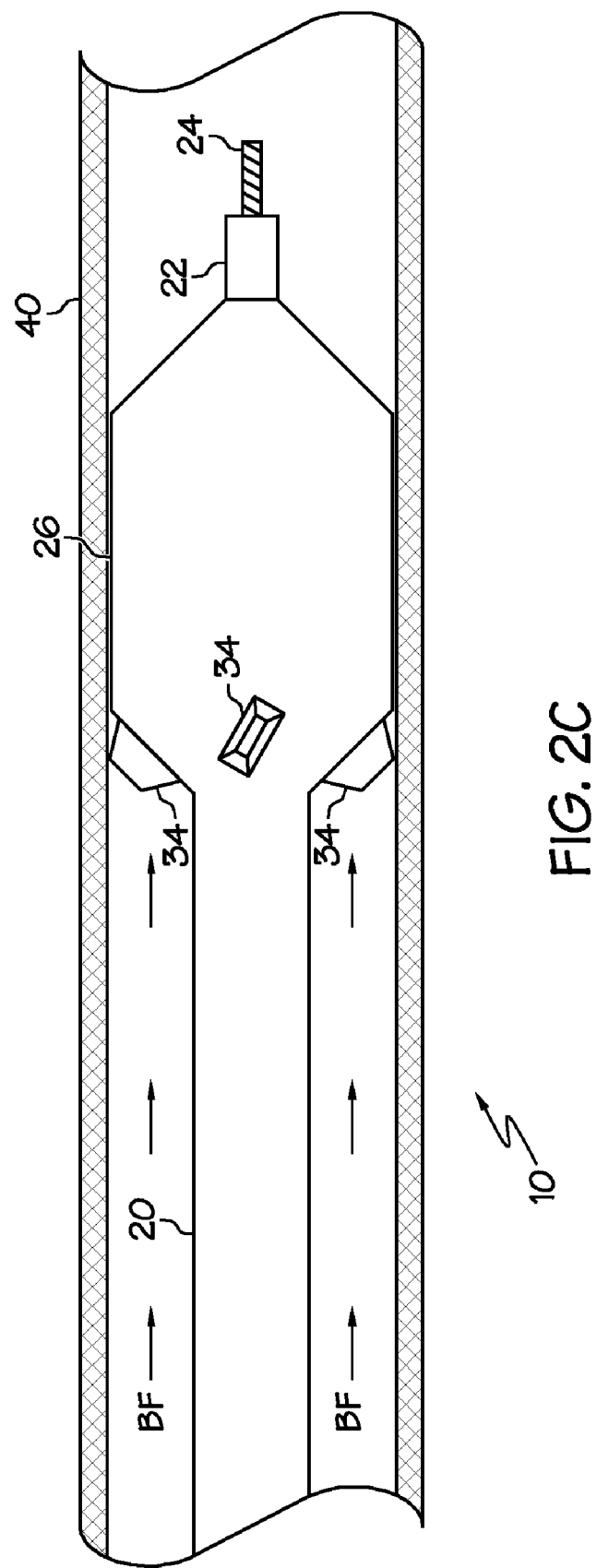
FIG. 2c is a cross-section of FIG. 2b with the balloon in an inflated state and the blood flow circling the catheter at the proximal end of the balloon.

FIGS. 2a-2d illustrate how the blood flow (BF) within the blood vessel 40 helps to rewrap the balloon catheter embodiment of FIG. 1c. In FIG. 2a, the blood vessel 40 has the balloon catheter 10 embodiment of FIG. 1c within it. The balloon 26 is in its non-expanded, pre-deployment state. The blood flow (BF) in the blood vessel 40 flows around the balloon catheter 10, as indicated by the arrows. In FIG. 2b, the balloon 26 has been inflated and the sides of the balloon 26 are engaged to the wall of the blood vessel 40. In at least one embodiment, because the balloon 26 is occluding the blood vessel 40, the blood flow (BF), as indicated by the arrows, forms an eddy in which the blood flow (BF) begins to circle the catheter shaft in either a clockwise direction or counter clockwise direction, as illustrated in FIG. 2c. In one embodiment, the angle of the fins 34 affects the direction of the blood flow.

Figure 2D:
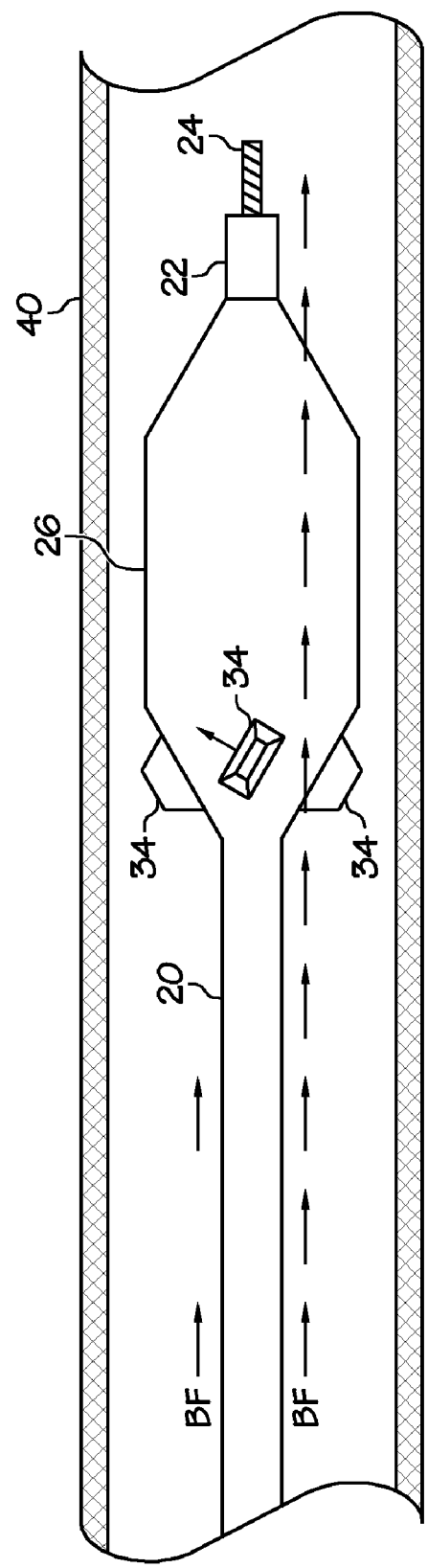
FIG. 2d is the cross-section of FIG. 2c with the balloon in a partially deflated state and the blood flow directed across the balloon by the fins.

Once the treatment with the balloon catheter 10 is completed, the balloon 26 is partially deflated by means known in the art, as illustrated in FIG. 2d. Once the balloon 26 is partially deflated, the blood flow (BF) past the balloon 26 is no longer inhibited. In at least one embodiment, fluid from the balloon catheter 10 is released into the blood stream at a point proximal to the balloon 26 so that the amount of fluid going past the balloon 26 is increased. In at least one embodiment, fluid is released from holes in the outer shaft 20. In at least one embodiment, fluid is released from holes in the proximal waist 28 of the balloon 26. In at least one embodiment, the fluid released from the balloon catheter 10 into the blood flow increases the pressure of the blood flow against the balloon 26.

Figure 2E:
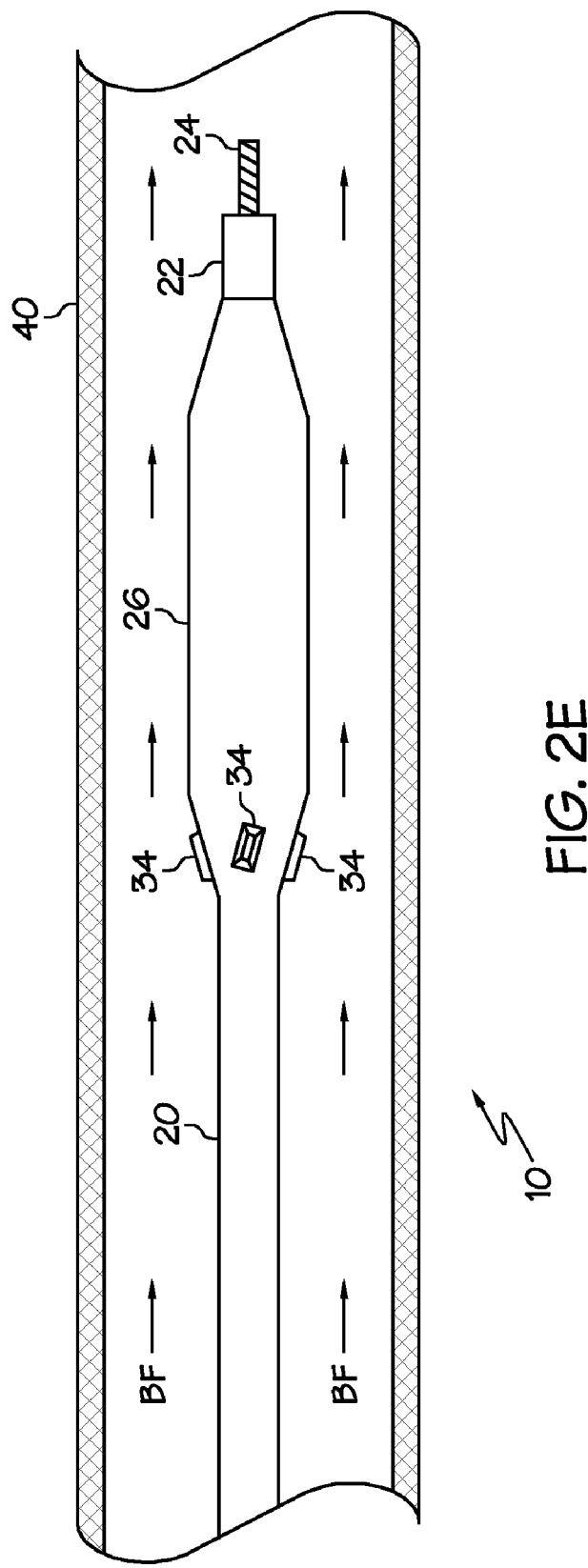
FIG. 2e is the cross-section of FIG. 2d with the balloon in a rewrapped state.

In at least one embodiment, due to the position of the fins 34 relative to the longitudinal axis of the balloon catheter 10, the blood flow (BF) flows in prescribed paths about the balloon 26. The channeling of the blood flow (BF), indicated by the double arrows, also increases the pressure of the blood flow against the balloon 26 along those pathways, due to the concentration of the blood flow (BF) into those particular pathways. In at least one embodiment, due to the position of the fins 34 relative to the longitudinal axis of the balloon catheter 10, as the blood flows past the balloon 26, the fins 34 move in a circumferential direction, as illustrated in FIG. 2d by the arrow indicating the movement of one of the fins 34. The circumferential movement of the fins 34 helps the balloon 26 to rewrap. FIG. 2e shows the balloon 26 in a rewrapped state.

Figure 3A:
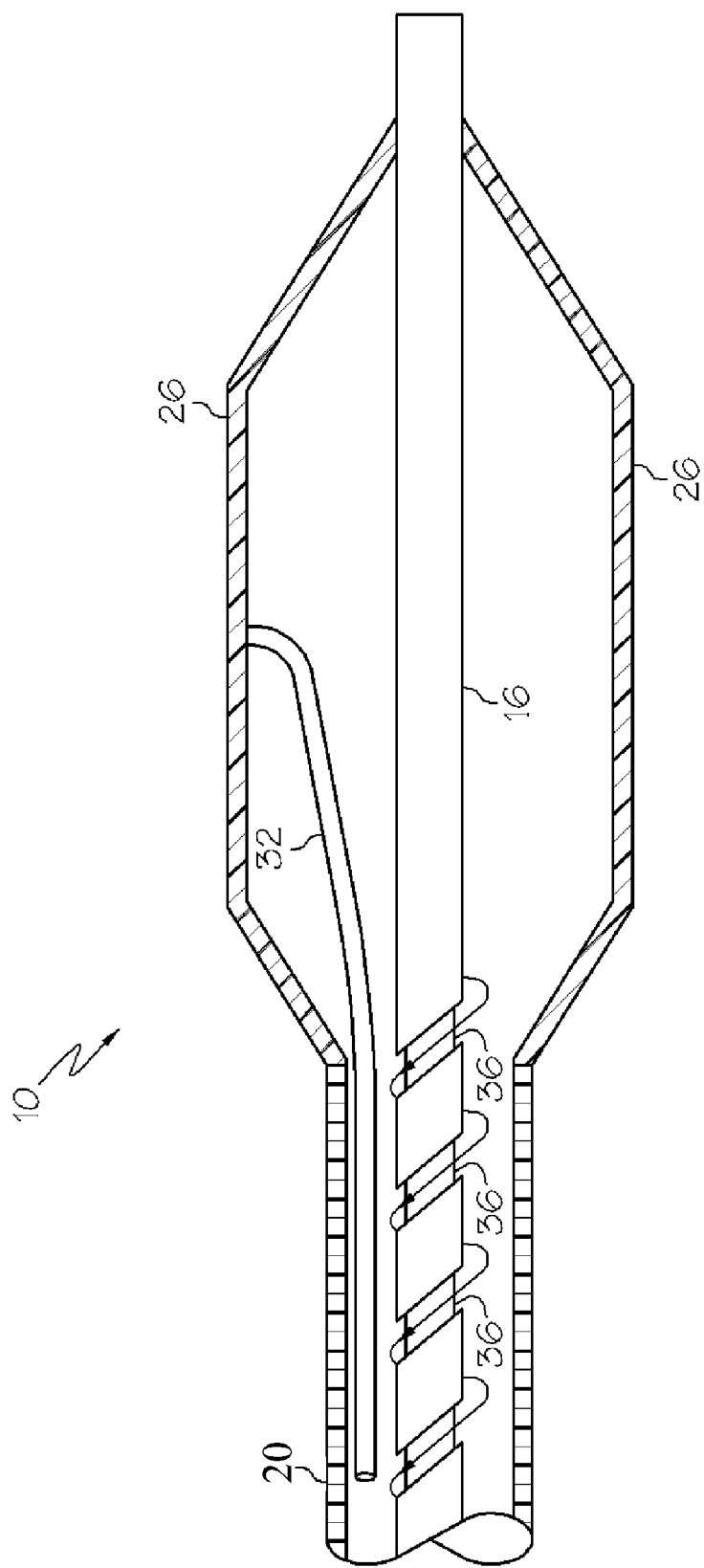
FIG. 3a is a longitudinal cross-section of a balloon catheter with at least one tether engaged to the interior surface of the balloon and the surface of the inner shaft has a flow channel.
Figure 3B:
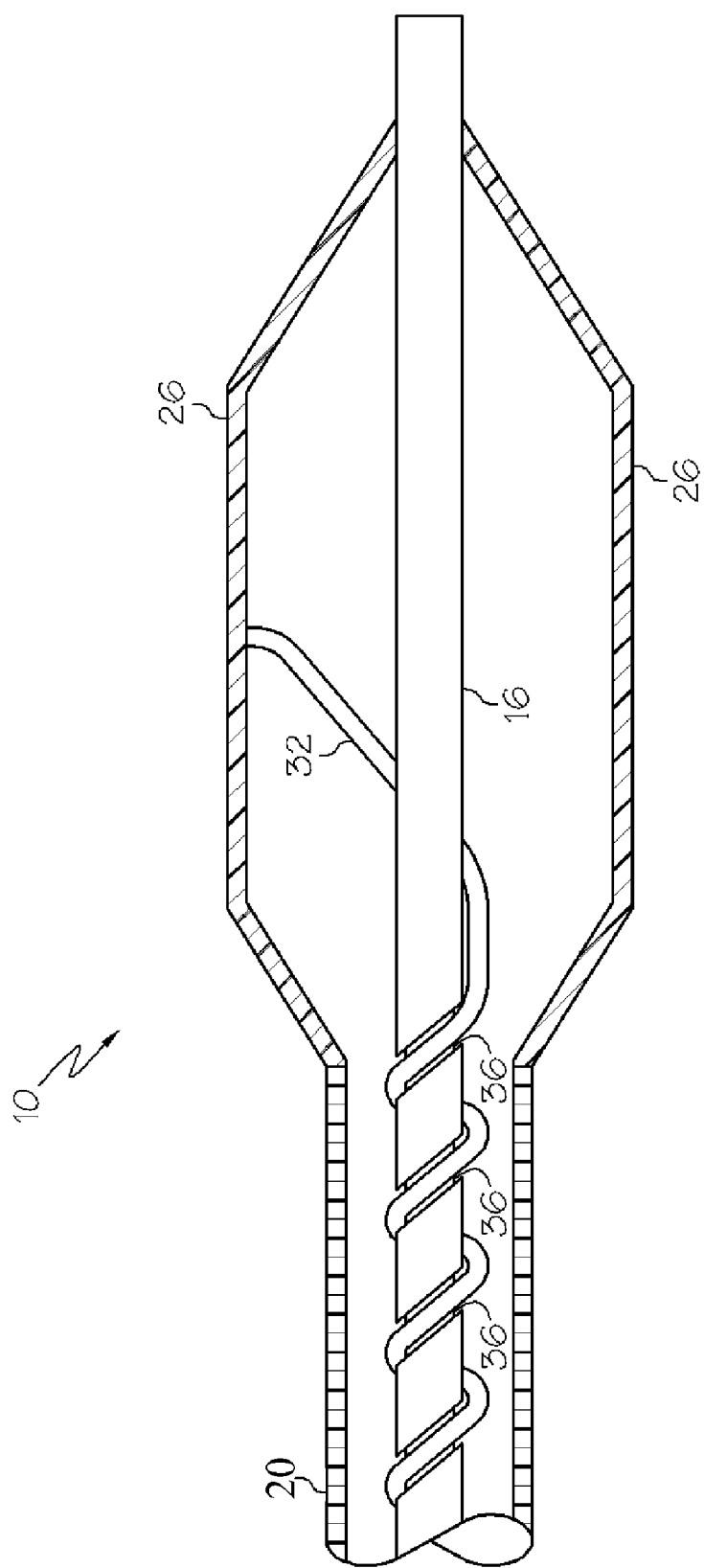
FIG. 3b is a longitudinal cross-section of the balloon catheter of FIG. 3a during the deflation of the balloon.

FIGS. 3a and b illustrates an embodiment of the balloon catheter 10 that has at least one tether 32 engaged to the interior surface of the balloon 26 and at least one flow channel 36 on the exterior surface of the inner shaft 16. The at least one flow channel 36 can extend along the longitudinal length of the inner shaft 16 for any length so long as it is sufficiently long to aid in balloon re-wrap, as discussed in greater detail below. In at least one embodiment, the flow channel 36 is helical, as illustrated in FIGS. 3a and 3b. As shown in FIG. 3a, the body of the inner shaft 16 defines the flow channel 36. Thus, the flow channel has two sides and a bottom defined by the inner shaft 16. Therefore, the inner shaft 16 has a variable outer diameter, with the portion of the inner shaft 16 having the flow channel 36 having an outer diameter that is less than the portion of the inner shaft 16 that does not have the flow channel 36. Additionally, the flow channel 36 has a depth, as shown in FIG. 3a. The depth can be described as being equal to the distance from the bottom of the flow channel 36 to the outer surface of the inner shaft 16.

Figure 3C:
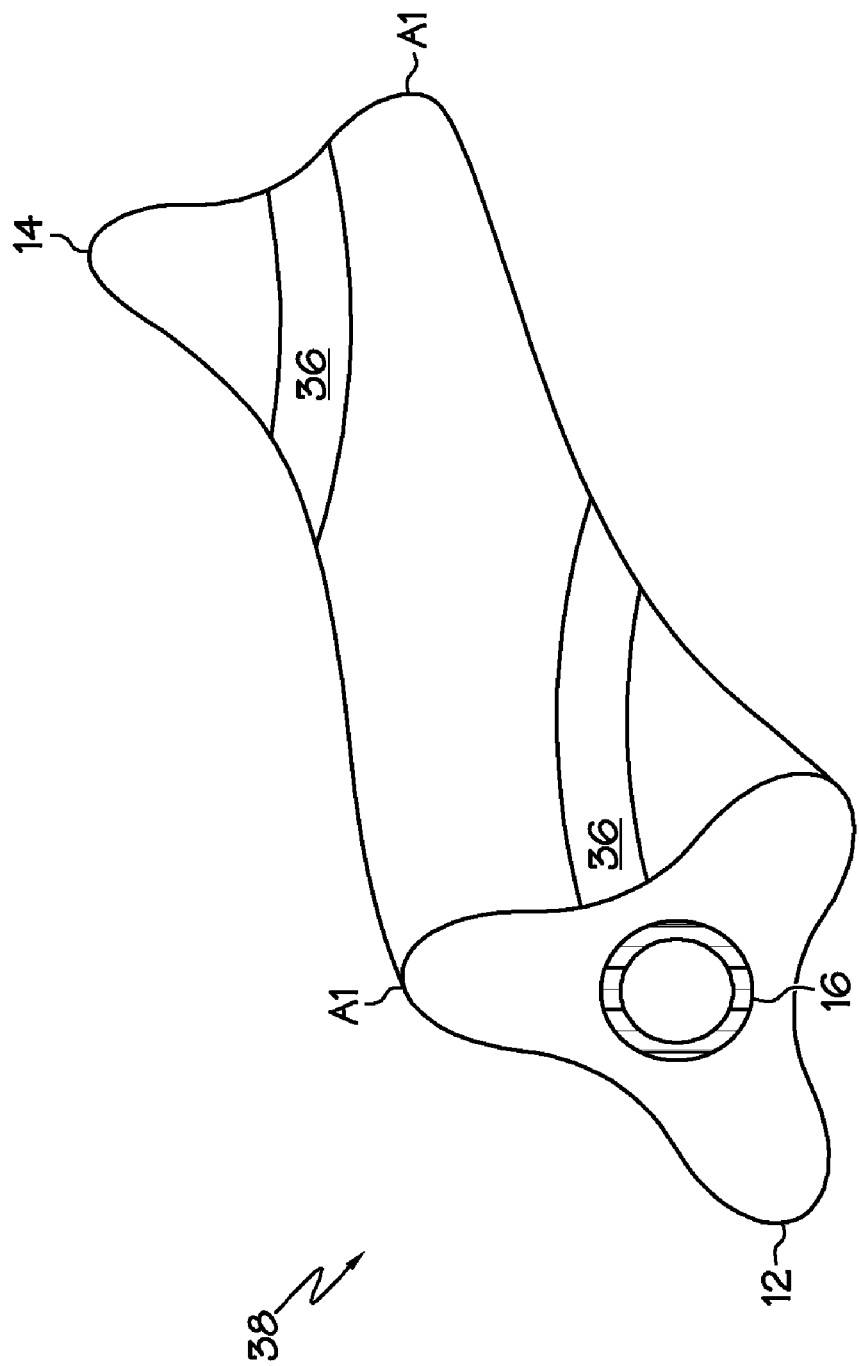
FIG. 3c is a perspective view of a collar engaged to the inner shaft of a balloon catheter.

In at least one embodiment, a collar 38 that defines at least one flow channel 36 is engaged to the inner shaft 16, as illustrated in FIG. 3c. The collar 38 can have any length and diameter so long as the dimensions are sufficiently large enough to define at least one flow channel 36 that aids in balloon rewrap, discussed in greater detail below. Thus, the collar 38 can have a length ranging from 1 mm to 1000 mm and a diameter ranging from 0.5 mm to 5 mm. In at least one embodiment, the outer surface of the collar 38 engages the inner surface of the outer shaft 20 so that the inflation lumen at the position of the collar 38 is the flow channels 36 in the outer surface of the collar 38 (not shown). In at least one embodiment, the collar 38 is manufactured from the same material as the inner shaft 16. In at least one embodiment, the collar 38 is manufactured from a different material than the inner shaft 16.

In FIG. 3c, the collar 38 has a twisted triangular shape so that the apexes, for example apex A1, extend in a helical manner from the distal end of the collar 38 to the proximal end of the collar 38. Between the apexes there are indentations which form the flow channels 36. In this embodiment, there are three flow channels 36 extending in a helical manner with a counter clockwise flow from the distal end 12 of the collar 38 to the proximal end 14 of the collar 38. Thus, it is within the scope of the invention for the balloon catheter 10 to have one, two, three, four, five, six or more flow channels 36 on the inner shaft 16, the collar 38, the balloon 26, and any combination thereof. Note that collar 38 can have any shape so long as it has at least one flow channel 36 which allows the inflation media to flow in either a clockwise or a counter clockwise direction. For example, in one embodiment, the collar 38 is substantially round and defines a flow channel 36 in the outer surface of the collar 38, similar to the inner shaft 16 of FIGS. 3a and 3b.

The balloon catheter 10 has at least one tether 32 engaged to the interior surface of the balloon 26. The tethers 32 can be engaged to the balloon 26 by any suitable means. It is within the scope of the invention for a tether 32 to be engaged to any portion of the balloon 26, e.g. body, cone, or waist so long as the tether 32 can facilitate re-wrap as discussed in greater detail below. In at least one embodiment, the area of the balloon 26 to which the tethers 32 are engaged is reinforced. In at least one embodiment, the tethers 32 are manufactured with mylar fibers or nylon fiber/thread. It is within the scope of the invention for the tethers 32 to have any configuration, for example, but not limited to, rope-like shape or a ribbon-like shape, so long as the tethers 32 facilitate re-wrap of the balloon 26. In at least one embodiment, the tethers 32 and the balloon 26 are manufactured from the same material.

Although for simplicity, FIGS. 3a and 3b illustrate only one tether 32, it is within the scope of the invention for there to be one, two, three, four, five, six, seven, eight, nine, ten or more tethers 32 engaged to the interior surface of the balloon 26. One end of the tether 32 is engaged to the interior surface of the balloon 26. The tethers 32 can be engaged to any location on the interior surface of the balloon 26 so long as the tethers 32 aid in the rewrap of the balloon 26, as explained in greater detail below. In one embodiment, tethers 32 are engaged to the distal portion of the balloon 26. In one embodiment, each of the tethers 32 is engaged about the circumference of the balloon 26 at one longitudinal position. In one embodiment, at least one of the plurality of tethers 32 is engaged to the interior surface of the balloon 26 at a different longitudinal position from the other tethers 32.

As is known in the art, inflation media is used to inflate the balloon 26. In order to deflate the balloon 26, the inflation media within the balloon 26 is evacuated or withdrawn from the balloon 26. As the inflation media is withdrawn, at least a portion the inflation media is drawn into the flow channel 36 and flows in either a clockwise or counterclockwise direction, depending upon the design of the flow channel 36. In one embodiment, all of the inflation media is directed/drawn into the flow channel 36. As shown in FIG. 3a, the flow channel 36 has a counter clockwise flow. This method of evacuating the inflation media from the balloon 26 is similar to the flow of water from a toilet bowl after it has been flushed.

As illustrated in FIG. 3b, the second end of the tether 32, the free end, is pulled in a proximal direction, about the inner shaft 16, by the inflation media as the inflation media is withdrawn from the balloon 26. Thus, the second end of the tether 32 wraps around the inner shaft 16, or collar 38 if a collar 38 is used, as the inflation media is withdrawn from the balloon 26, because at least a portion of the inflation media is flowing within the flow channel 36. As the free end of the tether 32 wraps around the inner shaft 16 and is being pulled in the proximal direction, the entire tether 32 is pulled down towards the inner shaft 16 thereby facilitating the re-wrap of the balloon 26 since the balloon 26, which is engaged to the tether 32, is also pulled down towards the inner shaft 16. In at least one embodiment, as the tethers 32 wind around the inner shaft 16, the length of the tethers 32 decreases, thereby pulling the interior of the balloon 26 towards the inner shaft 16. Another way to describe the action of a plurality of tethers 32 on the balloon 26 is that the tethers 32 look like fan blades as they wind around the inner shaft 16 as the inflation media is evacuated via the flow channel(s) 36 from the balloon 26 in a clockwise or counterclockwise manner.

The inner shaft 16 is manufactured from any suitable shaft material, for example, but not limited to, polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro (propyl vinyl ether) (PFA), polyether-ester, polymer/metal composites, etc., or mixtures, blends or combinations thereof. One example of a suitable polyether block ester is available under the trade name ARNITEL, and one suitable example of a polyether block amide (PEBA) is available under the trade name PEBAX®, from ATOMCHEM POLYMERS, Birdsboro, Pa.

The balloons 26 can be manufactured from any suitable balloon material. In at least one embodiment, the balloon is manufactured with semi-compliant material, for example, but not limited to, ethylene-vinyl acetate, polyvinyl chloride (PVC), olefin copolymers or homopolymers, polyethylenes, polyurethanes, crosslinked low density polyethylenes (PETs), highly irradiated linear low density polyethylene (LDPE), acrylonitrile polymers and copolymers, acrylonitrile blends and ionomer resins. In at least one embodiment, the balloon is manufactured with non-compliant material, for example, but not limited to, polyethylene terephthalates, polyacrylenesulfide, and copolyesters. In at least one embodiment, the balloon is manufactured with compliant material, for example, but not limited to, nylon, and polyamines. Other balloon materials may also be used.

In some embodiments, a portion of the balloon catheter 10 may include one or more areas, bands, coatings, members, etc. that is (are) detectable by imaging modalities such as X-Ray, MRI, ultrasound, etc. In some embodiments at least a portion of the balloon catheter 10 is at least partially radiopaque.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising-"means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A method of using a balloon catheter, comprising the steps of
providing a balloon catheter, the balloon catheter comprising an inner shaft, a balloon, at least one tether and at least one flow channel, the balloon having an inner surface, the at least one tether having a first end engaged to the inner surface of the balloon, the inner shaft having an outer surface, the at least one flow channel being a helical groove in the outer surface of the inner shaft;
inserting the balloon catheter into the vasculature;
advancing the balloon catheter through the vasculature to a desired location;
inflating the balloon with inflation media when the balloon catheter is at the desired location; and
removing the inflation media from the balloon, at least a portion of the inflation media flowing out of the balloon in the at least one flow channel.

2. The method of claim 1, the inflation media flowing out of the balloon in the at least one flow channel pulling the at least one tether, the at least one tether pulling at least a portion of the balloon towards the inner shaft.

3. A balloon catheter, the balloon catheter comprising an inner shaft, a balloon, at least one flow channel, and at least one tether, the balloon having an interior surface, the at least one tether comprising a first end engaged to the interior surface of the balloon and a second end that is not fixedly attached, the inner shaft having an outer surface, the at least one flow channel being helical groove in the outer surface of the inner shaft.

4. The balloon catheter of claim 3, the at least one flow channel having a depth, the depth of the at least one flow channel equal to the distance from the bottom of the at least one flow channel to the outer surface of the inner shaft.

5. The balloon catheter of claim 3, the balloon catheter further comprising an outer shaft, the inner shaft being positioned within the outer shaft, the outer shaft defining an inflation lumen in fluid communication with the balloon.

6. The balloon catheter of claim 5, the balloon comprising a first end engaged to the inner shaft and a second end engaged to the outer shaft.

7. The balloon catheter of claim 3, wherein the balloon catheter has a first state, in the first state, at least a portion of the at least one tether being disposed within the at least one flow channel.

8. The balloon catheter of claim 3, the at least one tether being a plurality of tethers, each tether having a longitudinal position and a circumferential position wherein the tethers have the same longitudinal position and the tethers have different circumferential positions.

9. A balloon catheter, the balloon catheter comprising an inner shaft, a balloon, a collar, and at least one tether, the balloon having an interior surface, the at least one tether comprising a first end engaged to the interior surface of the balloon and a second end that is not fixedly attached, a portion of the inner shaft disposed within and engaged to the collar, the collar having an outer surface, the at least one flow channel being a helical groove in the outer surface of the collar.

10. The balloon catheter of claim 9, the collar having a twisting triangular shape with a plurality of apexes each extending in a helical manner from a distal end of the collar to a proximal end of the collar.

11. The balloon catheter of claim 10, the at least one flow channel being three flow channels wherein each outer surface of the collar between adjacent pairs of apexes has one of the three flow channels.

12. The balloon catheter of claim 9, the collar having a cylindrical shape, the collar defining the at least one flow channel in an outer surface of the collar.

13. The balloon catheter of claim 12, the at least one flow channel having a depth, the depth of the at least one flow channel equal to the distance from the bottom of the at least one flow channel to the outer surface of the collar.

14. The balloon catheter of claim 9, the balloon catheter further comprising an outer shaft, the inner shaft being positioned within the outer shaft, the outer shaft defining an inflation lumen in fluid communication with the balloon.

15. The balloon catheter of claim 14, the balloon comprising a first end engaged to the inner shaft and a second end engaged to the outer shaft.

16. The balloon catheter of claim 9, wherein the balloon catheter has a first state, in the first state, at least a portion of the at least one tether being disposed within the at least one flow channel.

* * * * *